(12) United States Patent
McDermott

(10) Patent No.: US 10,159,559 B2
(45) Date of Patent: Dec. 25, 2018

(54) SINGLE LAYER EPTFE AND DISCRETE BIO-RESORBABLE RINGS

(71) Applicant: C. R. Bard, Inc., Murray Hill, NJ (US)

(72) Inventor: John D. McDermott, Coto De Caza, CA (US)

(73) Assignee: C. R. Bard, Inc., Murray Hill, NJ (US)

( * ) Notice: Subject to any disclaimer, the term of this patent is extended or adjusted under 35 U.S.C. 154(b) by 426 days.

(21) Appl. No.: 14/515,454

(22) Filed: Oct. 15, 2014

(65) Prior Publication Data
US 2015/0037493 A1 Feb. 5, 2015

Related U.S. Application Data

(62) Division of application No. 12/441,085, filed as application No. PCT/US2007/078359 on Sep. 13, 2007, now abandoned.

(60) Provisional application No. 60/845,295, filed on Sep. 18, 2006.

(51) Int. Cl.
| | |
|---|---|
| *A61F 2/07* | (2013.01) |
| *B05D 1/02* | (2006.01) |
| *B05D 3/00* | (2006.01) |
| *B05D 7/22* | (2006.01) |
| *A61F 2/82* | (2013.01) |
| *A61F 2/89* | (2013.01) |

(52) U.S. Cl.
CPC .................. *A61F 2/07* (2013.01); *B05D 1/02* (2013.01); *B05D 3/007* (2013.01); *B05D 7/22* (2013.01); *A61F 2/89* (2013.01); *A61F 2002/075* (2013.01); *A61F 2002/826* (2013.01); *A61F 2210/0004* (2013.01); *A61F 2240/001* (2013.01); *Y10T 29/49778* (2015.01); *Y10T 29/49838* (2015.01)

(58) Field of Classification Search
CPC ...... A61F 2/82; A61F 2/90; A61F 2/86; A61F 2/07; Y10T 29/49778
See application file for complete search history.

(56) References Cited

U.S. PATENT DOCUMENTS

| | | | | |
|---|---|---|---|---|
| 6,317,980 | B2 * | 11/2001 | Buck, III | B23Q 3/186 29/407.04 |
| 6,626,939 | B1 * | 9/2003 | Burnside | A61F 2/07 623/1.38 |
| 2002/0052649 | A1 * | 5/2002 | Greenhalgh | A61F 2/07 623/1.39 |
| 2005/0038501 | A1 * | 2/2005 | Moore, Jr. | A61F 2/91 623/1.15 |
| 2008/0009781 | A1 * | 1/2008 | Anwar | A61F 2/07 623/1.36 |
| 2008/0027534 | A1 * | 1/2008 | Edwin | A61F 2/07 623/1.44 |

FOREIGN PATENT DOCUMENTS

DE    10223399 A1 * 12/2003 ............. A61F 2/86

OTHER PUBLICATIONS

DE 10223399 translation.*

* cited by examiner

*Primary Examiner* — Brian Pellegrino
(74) *Attorney, Agent, or Firm* — Rutan & Tucker, LLP

(57) ABSTRACT

A stent-graft, including a generally tubular vascular graft of biocompatible material, and a plurality of bio-resorbable discrete annular members spaced apart along a longitudinal axis of the vascular graft and attached thereto.

8 Claims, 2 Drawing Sheets

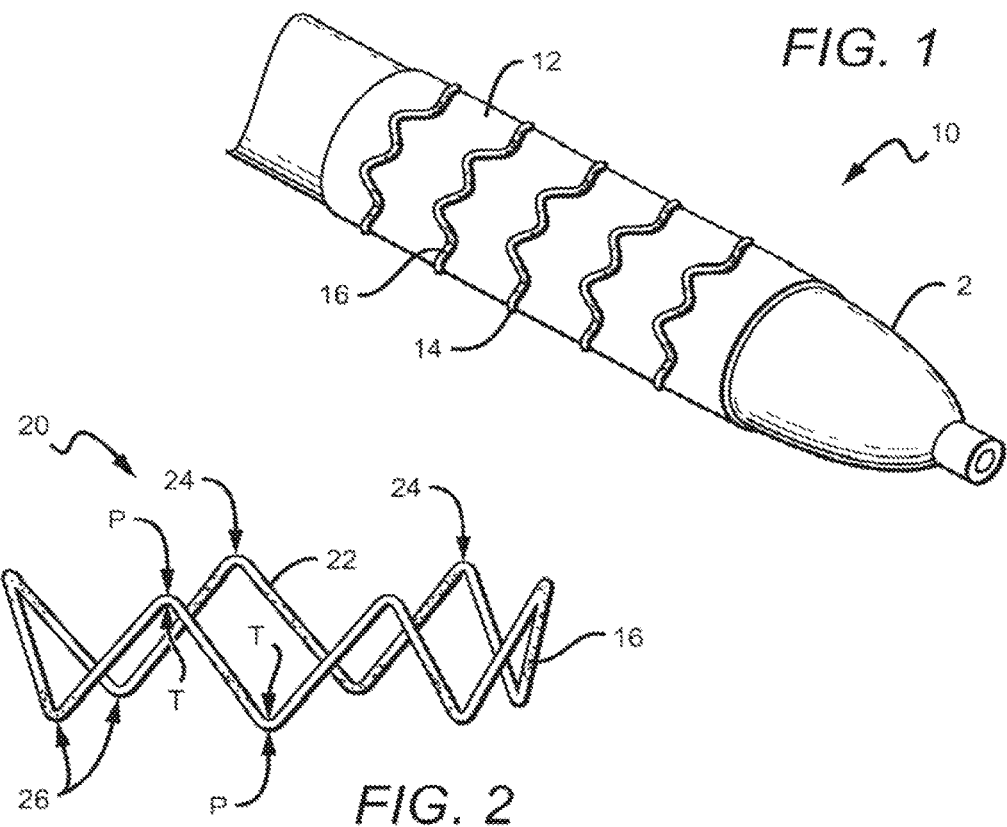
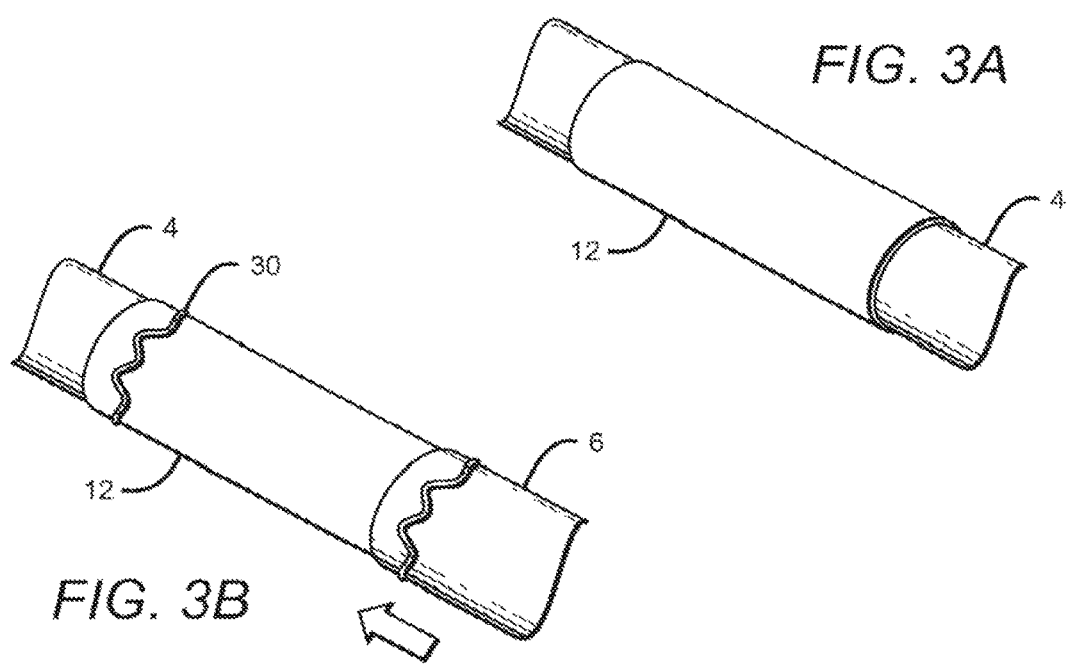

SINGLE LAYER EPTFE AND DISCRETE BIO-RESORBABLE RINGS

PRIORITY

This application is a division of U.S. application Ser. No. 12/441,085, filed Mar. 12, 2009, which is a U.S. national stage application under 35 USC § 371 of International Application No. PCT/US2007/078359, filed Sep. 13, 2007, which claims the benefit of priority to U.S. Provisional Patent Application No. 60/845,295, filed Sep. 18, 2006, each of which are incorporated by reference into this application as if fully set forth herein.

BACKGROUND

Intraluminal prostheses used to maintain, open, or dilate blood vessels are commonly known as stents. Stent constructions generally include lattice type cylindrical frames that define a plurality of openings. Common frameworks for stents include individual rings linked along the length of the stent by a linking member, a continuous helically wrapped member (that may include one or more linking members), a braid or a mesh formed into a tubular structure, and a series of interconnected struts. Stents are either self-expanding or balloon expandable. Self-expanding stents are delivered to a blood vessel in a collapsed condition and expand in vivo following the removal of a constraining force and/or in the presence of an elevated temperature (due to material properties thereof), whereas balloon expandable stents are generally crimped onto a balloon catheter for delivery and require the outwardly directed force of a balloon for expansion. Stents can be made of various metals and polymers. Stents can also be made of bioabsorbable materials, such as described in U.S. Pat. No. 6,245,103 to Stinson et al., which is incorporated by reference in its entirety into this application.

Synthetic vascular grafts are routinely used to restore the blood flow in patients suffering from vascular diseases. For example, prosthetic grafts made from expanded polytetrafluoroethylene (ePTFE) are commonly used and have shown favorable patency rates, meaning that depending on a given time period, the graft maintains an open lumen for the flow of blood therethrough. Grafts formed of ePTFE include a microstructure characterized by spaced apart nodes connected by fibrils, the distance between the nodes defined as internodal distance (IND).

It is known in the art to use stents in combination with vascular grafts to form stent-grafts. In one type of stent-graft, individual rings without a linking member are spaced apart along a length of the stent-graft. The rings may be encapsulated between two layers, such as described in U.S. Pat. No. 5,123,917 to Lee, or may be disposed on a surface of a graft, such as described in U.S. Pat. No. 6,364,903 to Tseng et al., each of which is incorporated by reference in its entirety into this application.

The following references relate to stent-grafts: U.S. Pat. No. 6,626,939, U.S. Pat. No. 6,733,524, U.S. Pat. No. 7,108,716 and U.S. Pat. No. 7,285,132, each of which is incorporated by reference in its entirety into this application.

Applicants have recognized that it would be desirable to provide a stent-graft including an ePTFE graft and discrete bio-resorbable members, embodiments of which are described herein along with methods of making same.

SUMMARY

Accordingly, in one embodiment, a stent-graft includes a generally tubular vascular graft of biocompatible material, and a plurality of discrete bio-resorbable annular members spaced apart along a longitudinal axis of the vascular graft and attached thereto.

In one embodiment, a method of making a stent-graft includes providing a plurality of discrete radially expandable annular members including a bio-resorbable balloon-expandable material, coating the annular members with a polyurethane material, positioning the coated annular members over a generally tubular expanded polytetrafluoroethylene vascular graft along a longitudinal axis thereof in spaced apart relation, and disposing a solvent between the coated annular members and the vascular graft.

In another embodiment, a method of making a stent-graft includes providing a plurality of discrete radially expandable bio-resorbable annular members, positioning the annular members over a generally tubular vascular graft along a longitudinal axis thereof in spaced apart relation, and weaving portions of the annular members into the base layer and attaching the annular members to the base layer with bio-resorbable sutures.

In one embodiment of a stent-graft and delivery system, the delivery system includes a balloon catheter and an outer sheath, the stent-graft is positioned over a balloon of the balloon catheter, the outer sheath is positioned over the stent-graft, and the stent-graft includes a generally tubular vascular graft of biocompatible material and a plurality of discrete radially expandable bio-resorbable annular members spaced apart along a longitudinal axis of the vascular graft and attached thereto.

In one embodiment, a method of treating a blood vessel includes providing a balloon catheter including a balloon on a distal end thereof and a stent-graft positioned over a length of the balloon, the stent-graft including a generally tubular vascular graft of biocompatible material and a plurality of discrete radially expandable bio-resorbable annular members spaced apart along a longitudinal axis of the vascular graft and attached thereto, inserting the balloon catheter in a blood vessel, navigating the balloon to a predetermined region of the blood vessel, and inflating the balloon to bring a surface of one or more of the annular members in contact with the blood vessel wall.

In one embodiment, a method of loading a stent-graft in a sheath includes forming a stent-graft, including positioning a plurality of discrete annular bio-resorbable members along a surface of an ePTFE graft, the annular members spaced apart along a longitudinal axis of the ePTFE graft and attached thereto, the annular members having an expanded configuration defining an expanded perimeter, compressing the stent-graft, the annular members collapsing to a collapsed configuration defining a collapsed perimeter smaller than the expanded perimeter, and positioning a sheath over the stent-graft, the sheath maintaining the annular members in the collapsed configuration.

These and other embodiments, features and advantages will become more apparent to those skilled in the art when taken with reference to the following more detailed description of the invention in conjunction with the accompanying drawings that are first briefly described.

BRIEF DESCRIPTION OF THE DRAWINGS

FIG. 1 is a perspective view of an embodiment of a stent-graft with discrete annular members loaded onto an expandable member.

FIG. 2 is a perspective view of one embodiment of a discrete annular member in isolation.

FIGS. 3A-C are perspective views of separate stages of making one embodiment of a stent-graft with discrete annular members.

DETAILED DESCRIPTION

Figure 3C:
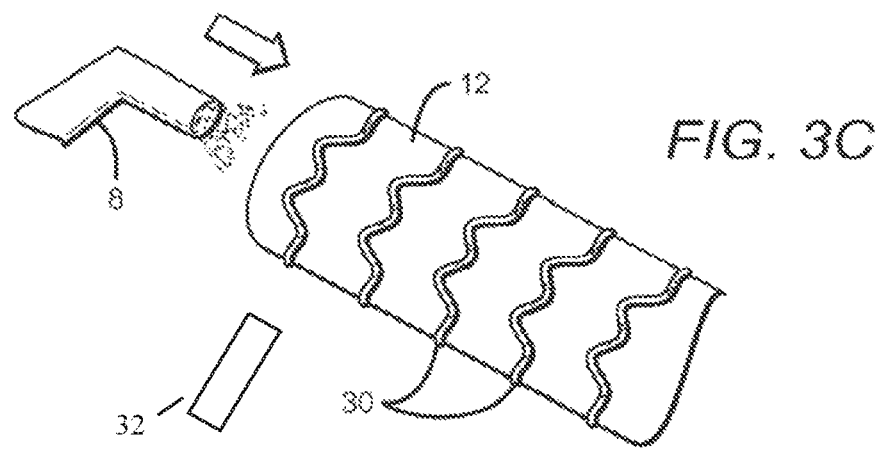

The following description should be read with reference to the drawings, in which like elements in different drawings are identically numbered. The drawings, which are not necessarily to scale, depict selected embodiments and are not intended to limit the scope of the invention. The description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

The stent-graft described herein may be utilized with bio-active agents to control the formation of emboli. Bio-active agents can be coated onto a portion or the entirety of the stent and/or graft for controlled release of the agents once the stent-graft is implanted. Bio-active agents can be added to the prosthesis (e.g., either by a coating or via a carrier medium such as resorbable polymers) for delivery to the host's vessel or duct. The bio-active agents may also be used to coat the entire stent, stent-graft or the graft. A coating may include one or more non-genetic therapeutic agents, genetic materials and cells and combinations thereof as well as other polymeric coatings.

Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/antimiotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants, an RGD peptide-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, cell cycle inhibitors and activators inhibitory antibodies, antibodies directed against growth factors, bifunctional molecules consisting of a growth factor and a cytotoxin, bifunctional molecules consisting of an antibody and a cytotoxin; cholesterol-lowemember agents; vasodilating agents; cytostatic or cytotoxic and agents which interfere with endogenous vascoactive mechanisms.

Genetic materials include anti-sense DNA and anti-sense RNA as well as other molecules working via the same mechanism of transcriptional or translational inhibition or activation. Genetic material also include (sense) DNA or (sense) RNA or equivalents thereof coding for Genes to replace defective or deficient endogenous molecules or increase their amount or stability, or encode for non-endogenous or endogenous modified molecules with biological effects. Genetic material also includes nucleic acids affecting Gene expression or other cellular mechanisms by other ways than described above. Such Genetic materials could be organized "naked," packed with supporting molecules or in form of viruses or other vectors. Genes and their expression affected by above Genetic materials include but are not restricted to: tRNA or rRNA angiogenic factors including growth factors such as acidic and basic fibroblast growth factors, vascular endothelial growth factor, epidermal growth factor, transforming growth factor alpha and beta, platelet-derived endothelial growth factor, platelet-derived growth factor, tumor necrosis factor alpha, hepatocyte growth factor and insulin like growth factor, cell cycle inhibitors and activators including CD inhibitors, thymidine kinase ("TK") and other agents useful for interfemember with cell proliferation, transcription factors, translation factors, the family of bone morphogenic proteins ("BMP's"), BMP-2, BMP-3, BMP-4, BMP-5, BMP-6 (Vgr-1), BMP-7 (OP-1), BMP-8, BMP-9, BMP-10, BMP-1, BMP-12, BMP-13, BMP-14, BMP-15, and BMP-16. Desirable BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Cells can be of human origin (autologous or allogeneic) or from an animal source (xenogeneic), genetically engineered if desired to deliver proteins of interest at the deployment site. The cells may be provided in a delivery media. The delivery media may be formulated as needed to maintain cell function and viability.

Suitable polymer materials as a coating or the base material may include polycarboxylic acids, cellulosic polymers, including cellulose acetate and cellulose nitrate, gelatin, polyvinylpytrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides including cellulose, chitin, dextran, polyesters including polyethylene terephthalate, polyacrylamides, polyethers, polyether sulfone, polycarbonate including tyrosine-derived polycarbonate, polyalkylenes including polypropylene, polyethylene and high molecular weight polyethylene and poly(butylene terephthalate) (PBT), halogenated polyalkylenes including polytetrafluoroethylene, polyurethanes, polyorthoesters, proteins (including fibrin und casein), polypeptides, silicones, siloxane polymers, polylactic acid (PLA), polyglycolic acid (PGA), poly(lactide-co-glycolide) (PLGA) polycaprolactone, polydioxanone, poly(g-ethyl glutamate), poly(DTH iminocarbonate), poly(bisphenol A iminocarbonate), poly(ortho ester), polycyanoacrylate, and polyphosphazene, polyhydroxybutyrate valerate and blends and copolymers thereof, coatings from polymer dispersions such as polyurethane dispersions (for example, BAYHDROL® fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No.

5,091,205, the disclosure of which is incorporated by reference in its entirety into this application, is particularly desirable.

One suitable bioabsorbable material for the stent as described herein can be one or more of a metal alloy shown and described in U.S. Pat. No. 6,287,332, or the metal alloy shown and described in U.S. Patent Application Publication No. 2002/0004060, each of which is incorporated by reference in its entirety into this application. Preferably, the metallic bioabsorbable material is selected from a first group consisting essentially of: magnesium, titanium, zirconium, niobium, tantalum, zinc, silicon, and combinations thereof. Also provided are mixtures and alloys of metallic bioabsorbable materials, including those selected from the first group. Various alloys of the materials in the first group can also be used as a metallic bioabsorbable material, such as a zinc-titanium alloy, for example, as discussed in U.S. Pat. No. 6,287,332 to Bolz et al., which is incorporated by reference in its entirety into this application. The physical properties of the alloy can be controlled by selecting the metallic bioabsorbable material, or forming alloys of two or more metallic bioabsorbable materials. For example, the percentage by weight of titanium can be in the range of about 0.1% to about which can reduce the brittle quality of crystalline zinc. Without being bound to theory, it is believed that the addition of titanium leads to the formation of a $Zn_{15}Ti$ phase. In another embodiment, gold can be added to the zinc-titanium alloy at a percentage by weight of about 0.1% to about 2%, which is believed to result in a further reduction of the grain size when the material cures and further improving the tensile strength of the material.

In some embodiments, the metallic bioabsorbable material can be an alloy of materials from the first group and a material selected from a second group consisting essentially of: lithium, sodium, potassium, calcium, iron, manganese, and combinations thereof. The metallic bioabsorbable material from the first group can form a protective oxide or passivation coating upon exposure to blood or interstitial fluid. The material from the second group is preferably soluble in blood or interstitial fluid to promote the dissolution of the oxide coating. Also provided are mixtures and alloys of metallic bioabsorbable materials, including those selected from the second group and combinations of materials from the first group and the second group.

Briefly, the combination of metal materials can be a metal alloy, the selection of the alloy constituents (as explained in detail below) serving to attain the prerequisite of biocompatible decomposition. Consequently, the metal alloy may consist of a combination of material that will decompose in the body comparatively rapidly while forming harmless constituents. Such alloy may include a component A which covers itself with a protective oxide coating. This component A is selected from one or several metals of the group of magnesium, titanium, zirconium, niobium, tantalum, zinc, silicon, or combinations thereof. For uniform dissolution of the mentioned oxide coat to be attained, a component B is added to the alloy, possessing sufficient solubility in blood or interstitial fluid, such as lithium sodium, potassium, calcium, iron or manganese. The corrosion rate is adjusted by way of the composition so that gases, such as hydrogen, which evolve during the corrosion of lithium, sodium, potassium, magnesium, calcium or zinc, dissolve physically and essentially not forming any macroscopic gas bubbles. Other alloys can be utilized such as, for example, alloy of lithium and magnesium in the ratio of about 60:40; a sodium-magnesium alloy; a zinc-titanium alloy—the percentage by weight of which is in the range of about 0.1% to about 1% with the gold being optionally added at a percentage by weight of about 0.1% to about 2%. Further details relating to these metallic bioabsorbable materials are found in U.S. Pat. No. 6,287,332 to Bolz et al.

Other materials for the stent as described herein can include biodegradable polymers including shape memory polymers, such as, for example, polylactic acid, i.e., PLA, polyglycolic acid, i.e. PGA, polydioxanone, i.e., PDS, polyhydroxybutyrate, i.e., PHB, polyhydroxyvalerate, i.e., PHV and copolymers or a combination of PHB and PHV (available commercially as Biopol®), polycaprolactone (available as Capronor®), polyanhydrides (aliphatic polyanhydrides in the back bone or sick chains or aromatic polyanhydrides with benzene in the side chain), polyorthoesters, polyaminoacids (e.g., poly-L-lysine, polyglutamic acid), pseudo-polyaminoacids (e.g., with back bone of polyaminoacids altered), polycyanocrylates, or polyphosphazenes.

As used herein, the term "bio-resorbable" includes a suitable bio-compatible material, mixture of materials or partial components of materials being degraded into other generally non-toxic materials by an agent present in biological tissue (i.e., being bio-degradable via a suitable mechanism, such as, for example, hydrolysis) or being removed by cellular activity (i.e., bioresorption, bioabsorption, or bioresorbable), by bulk or surface degradation (i.e., bioerosion such as, for example, by utilizing a water insoluble polymer that is soluble in water upon contact with biological tissue or fluid), or a combination of one or more of the bio-degradable, bio-erodable, or bio-resorbable material noted above.

Referring now to FIG. 1, a stent-graft 10 is shown disposed over an inflatable member 2 on a distal end of a catheter, such as a balloon catheter. The stent-graft 10 includes a generally tubular vascular graft 12 and discrete annular members 14 spaced apart along a longitudinal axis of the graft 12, the graft 12 providing a base member or substrate for the annular members 14. The vascular graft 12 may be made of a polymeric material, such as, for example, Dacron, nylon, polyester, polyurethane and fluoropolymers, such as perfluoroelastomers and the like, but in the preferred embodiment is made of expanded polytetrafluoroethylene (ePTFE). As known in the art, an ePTFE vascular graft may be manufactured in a number of ways, including, for example, extrusion of a tube (seamless), extrusion of a sheet that is subsequently thrilled into a tube (one or more seams), helical wrapping of ePTFE tape around a mandrel (e.g., multiple seams or preferably a single helical seam), etc. The preferred method used for forming an ePTFE vascular graft in the present invention is extrusion of a generally tubular member. Extrusion and expansion of the tubular member may be controlled to provide a range of internodal distances. In a preferred embodiment, the average internodal distance is in the range of approximately 10 microns to approximately 110 microns.

While the discrete annular members 14 may be made of a self-expanding or balloon expandable material, in the embodiment shown in FIG. 1, the annular members 14 are made of a balloon expandable bio-resorbable material, such as any of those discussed above. In one embodiment, the annular members 14 include a coating 16. The coating 16 may cover substantially the entire surface area of the annular members or may only cover a portion thereof. In a preferred embodiment, the annular members 14 include a coating that covers at least the portion in contact with the vascular graft 12 to assist with attachment of the annular members 14 with the vascular graft 12. The coating may include a polymer that is capable of adhering to the vascular graft 12, through the application of for example, heat, pressure, solvents, adhesives (e.g., bio-resorbable adhesives), or combinations thereof. Suitable polymers for the coating may include, for example, polytetrafluoroetlaylene (PTFE), ePTFE polyurethane, fluorinated ethyl propylene (FEP), an amorphous fluoropolymer, and combinations thereof. In a preferred embodiment, the polymer includes an amorphous fluoropolymer including tetrafluoroethylene (TEF) and 4,5-difluoro-2,2-bis(trifluormethyl)-1,3-dioxole, or a perfluoroelastomer, as described in U.S. Patent Application Publication No. 2005/0131527, which is incorporated by reference in its entirety into this application. The coating may have a thickness in the range of approximately 1 micron to approximately 100 microns. The coating may be in the form of particles or powder, and may be applied to the annular members 14 and/or to the vascular graft 12 by spraying, dip coating, or other methods known to one skilled in the art. In one embodiment, the coating is a fluoropolymer including TEF in powdered form which is disposed directly on a surface of the vascular graft 12 so that when the annular members 14 are positioned on the surface, the powder is positioned between the vascular graft 12 and a surface of one or more annular members 14.

Referring to FIG. 2, one embodiment of an annular member 20 is illustrated. Annular member 20 includes struts 22 arranged in an undulating configuration that is preferably closed ended. The struts 22 intersect at an apex to form a first set of apices 24 and a second set of apices 26 offset therefrom, such that annular member 20 includes an equal number of first and second apices 24, 26. Each apex includes a peak P and a trough T. The lengths of the struts 22 may be uniform, as shown, or may be varied about the circumference of the annular member. For example, the annular member could include two or more strut lengths arranged in patterns about its circumference. Many other annular member configurations are also possible and are within the scope of the invention, such as, for example, sinusoidal patterns, meandering curve patterns, other curvilinear patterns, etc. The struts may be substantially straight along their lengths, as shown, or may be curved or wave-like. Any type of pattern and or strut length or shape can be combined with other patterns and/or strut lengths or shapes to form a non-uniform annular member Moreover, it should be appreciated that the shape, size, thickness, material and/or other characteristic of the annular members can be varied along the length of the stent-graft. Further, the undulations are not limited to zig-zag patterns but can be wave-like in pattern. The wave-like pattern can also be generally sinusoidal in that the pattern may have the general form of a sine wave, whether or not such wave can be defined by a mathematical function. Alternatively, any wave-like forms can be employed so long as it has amplitude and displacement. For example, a square wave, saw tooth wave, or any applicable wave-like pattern defined by the struts where the struts have substantially equal lengths or unequal lengths.

In one embodiment, annular members 20 are positioned along a surface of a vascular graft 12 so that the peak P of a first annular member 20 is aligned with a trough T of an adjacent annular member 20, the adjacent annular members 20 being spaced a sufficient distance apart to prevent interference between the annular members 20 upon radial compression of the stent-graft. For example, the annular members 20 may be attached to a vascular graft in an expanded configuration defining an expanded perimeter of the annular members 20 and are subsequently radially compressed for delivery to a blood vessel to a collapsed configuration, defining a collapsed perimeter of the annular members 20 smaller than the expanded perimeter of the annular members 20. The sufficient distance between adjacent annular members to prevent interference is dependent on a variety of factors, such as, for example, length, shape, mind/or other characteristics of the struts, but in a preferred embodiment with annular members 30 having a uniform strut length of approximately 500 microns to approximately 1500 microns and having peaks P and troughs T of adjacent annular members 20 aligned, a sufficient distance between adjacent annular members 20 is in the range of approximately 0.1 millimeter to approximately 1 millimeter. In other embodiments, adjacent annular members 20 may have peaks P and/or troughs T offset circumferentially to each other.

Markers M1, M2, M3, M4 . . . Mn can be provided for all of the embodiments described herein. The marker Mn can be formed from the same material as the stent as long as the material is radiographic or radiopaque. The marker material can also be formed, for example, from gold, tantalum, platinum, and combinations thereof. One or more markers can be formed from a marker material different from other markers.

Attachment of the annular members to the vascular graft may be accomplished by various methods, which can be facilitated by the materials chosen for the annular members, vascular graft and/or coatings, if utilized. In a preferred embodiment illustrated in FIGS. 3A-C, an ePTFE vascular graft 12 is positioned over a mandrel 4. The ePTFE graft 12 may be sintered, unsintered, or partially sintered, but in a preferred embodiment, the ePTFE graft 12 is sintered. Using a loading tool 6, a predetermined number of annular members 30 with a polyurethane coating are positioned along the outer (abluminal) surface of the ePTFE graft 12. In a preferred embodiment, there are approximately 5 to approximately 100 annular members 30 positioned over an ePTFE graft having a length in the range of approximately 10 millimeters to approximately 200 millimeters. In one embodiment, the annular members 30 are pre-dilated (expanded) by the tool 6 for moving into position on an outer surface of the ePTFE graft 12. Depending on the material properties of the annular members 30, an additional crimping step may be required to secure the annular members in position. Once the annular members are initially positioned on a surface of the graft 12, a laser alignment fixture 32 is optionally utilized to optimally space the adjacent annular members with respect to one another.

The mandrel 4 is then removed from the assembly and the inside surface of the ePTFE graft 12 is sprayed, as depicted in FIG. 3A, with a solvent, such as tetrahydrofuran (THF), so that the THF migrates through the wall of the ePTFE graft. The spraying may be accomplished using different methods known to one skilled in the art. For example, the graft 12 may be suspended such that a lumen of the graft 12 is accessible; a spraying mechanism 8 is then inserted into the lumen and rotated to contact THF with a surface of the lumen. The entire surface of the lumen may be covered or select portions thereof. Alternatively, a mandrel with openings may be inserted into the lumen, the mandrel attached to a source of THF, where the THF is delivered to the mandrel and through the openings to contact a surface of the graft 12. Another possibility includes utilizing a needle device attached to a source of THF and inserting the needle through the wall of the graft 12 at various locations, where THF is delivered through the needle at each location to contact a surface of the lumen. The interaction between the ePTFE, THF and polyurethane coating on the annular members 30 bonds the annular members 30 to the ePTFE graft 12 (the THF or other aprotic solvent is believed, to dissolve polyurethane, such that when a small amount contacts the polyurethane coating, a mechanical bond is developed between the coating and the ePTFE graft 12).

In another embodiment, a suitable solvent, such as, for example, an aprotic solvent including dimethylacetamide (DMSE), dimethylforamide, THF, or their mixtures, is sprayed or otherwise disposed over the outside surface of the ePTFE graft 12 after the annular members 30 have been positioned thereover. Alternatively, the ePTFE graft 12 with annular members 30 could be dip coated in a suitable solvent. In another embodiment, the annular members 30 are positioned over an inner (luminal) surface of the ePTFE graft 12 prior to spraying of the solvent over the outer surface or inner surface of the ePTFE graft 12. In yet another embodiment, the annular members 30 are coated with PTFE and the ePTFE graft 12 is initially unsintered. Following placement of the annular members 30 over the graft 12, the assembly is heated above the crystalline melt point of PTFE to sinter the annular members 30 to the graft 12. Although the preferred embodiments are directed to single layer vascular grafts, it is within the scope of the invention to provide two or more graft layers. For example, the annular members could be disposed between two generally tubular graft layers, the graft layers being continuous along their length; the annular members could be disposed between two generally tubular graft layers, at least one of the graft layers including openings, as shown and described in U.S. Pat. Nos. 6,398,803 and 6,770,087 to Layne et al., which is incorporated by reference in its entirety into this application; or the annular members could he disposed between a generally tubular graft layer and strips and bands of covering material, such as shown and described in U.S. Pat. No. 6,558,414 to Layne, which is incorporated by reference in its entirety into this application. Other stent-graft arrangements with respect to covering material and annular members known to one skilled in the art are also contemplated herein.

Figure 4:
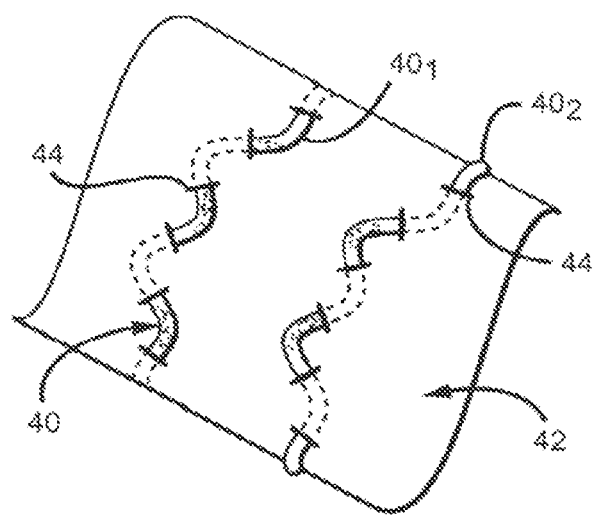
FIG. 4 is an enlarged perspective view of another embodiment of a stent-graft with discrete annular members.

In one attachment method, annular members 40, which may or may not include a coating, are woven into a vascular graft 42. In one embodiment, shown in FIG. 4, the annular members 40, having a zig-zag configuration with struts intersecting at first apices and second apices offset from the first apices, are woven into the vascular graft 42. In a preferred embodiment, the vascular graft 42 is made of ePTFE. As illustrated, the peaks and troughs of the annular members 40 are generally aligned, with the first apices of adjacent annular members 40 disposed on opposite surfaces of the vascular graft 42. For example, if the first apices of annular members 40$_1$ are disposed on the inside surface of the vascular graft 42, then the first apices of annular members 40$_2$ are disposed on the inside surface of the vascular graft 42. Bio-resorbable sutures 44 are utilized in the embodiment of FIG. 4 to attach the annular members 40 to the vascular graft 42. The sutures 44 may be positioned around each apex of the annular members 40, every other apex, every apex of the first apices, every apex of the second apices, at a mid point of each strut, at a mid-point of every second, third, fourth, etc. strut, at locations where the strut passes through the wall of the vascular graft 42, or any other pattern or arrangement that would prevent pre-mature detachment of the annular members 40 from the vascular graft 42. In certain embodiments, additional attachment methods are utilized in conjunction with the sutures 44, such as, for example, spraying with a solvent, such as THF (e.g., the annular members 40 include a coating, such as polyurethane), disposing an adhesive, such as a bio-resorbable adhesive, over one or more surfaces of the vascular graft 42 (e.g., at locations of contact with the annular members 40), heating the stent-graft (e.g., the ePTFE is unsintered and the annular members 40 include a coating, such as PTFE), applying a uniform pressure to the assembled stent-graft along both inner and outer surfaces, or any combination thereof.

Referring back to FIG. 1, the annular members 14 include a balloon expandable bio-resorbable material and are attached to the vascular graft 12 in an original or non-expanded configuration with a original perimeter. In one embodiment of treating a blood vessel, the stent-graft 10 is positioned over a length of the balloon 2 of the balloon catheter, which may be a component of a delivery system (e.g. the balloon catheter may be coaxially disposed in an outer sheath), and the balloon catheter/delivery system is inserted intraluminally in a patient to a predetermined region of a blood vessel. The balloon is then inflated to expand the stent-graft, the annular members 14 expanding to an expanded configuration with an expanded perimeter larger than the original perimeter, to bring a surface of one or more of the annular members in contact with the blood vessel wall. After positioning is confirmed, the balloon is deflated and the balloon catheter removed from the blood vessel.

In another embodiment, the annular members include a self-expanding bio-resorbable material and are attached to a vascular graft in an expanded configuration defining an expanded perimeter. The stent-graft is then compressed, the annular members collapsing to a collapsed configuration with a collapsed perimeter smaller than the expanded perimeter. A constraining sheath, which may be a component of it delivery system, is positioned over the stent-graft to maintain the annular members in the collapsed configuration and the sheath is delivered intraluminally in a patient to a predetermined region of a blood vessel. The constraining sheath is then removed from the stent-graft, allowing the annular members to expand such that one or more annular members have a surface in contact with the blood vessel wall. A balloon can optionally be inserted and inflated thereafter to ensure contact with the blood vessel wall and positioning of the stent-graft in the blood vessel.

Following deployment of a stent-graft with bio-resorbable annular members in as blood vessel, the annular members will begin to degrade, while the vascular graft is designed to remain permanently implanted (although slight degradation to the graft may take place over time). The time for degradation of the annular members will depend on a number of factors, including, for example, member material, member thickness, member surface area, the type and thickness of the coating (if utilized), etc. In the preferred embodiments, the bioresorption is configured to be from 3 months to 2 years for complete resorption.

This invention has been described and specific examples have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A method of making a stent-graft comprising:
providing a plurality of individual, radially expandable, annular members made from a bioresorbable material capable of being expanded by a balloon;
coating the annular members with a polyurethane material;
positioning the annular members in a consecutive adjacent, spaced-apart relation over a tubular expanded polytetrafluoroethylene vascular graft along a longitudinal axis of the vascular graft such that the members avoid adjacent members upon radial compression of the stent-graft; and
disposing a solvent between the annular members and the vascular graft.

2. The method of claim 1, wherein the solvent is THF.

3. The method of claim 2, wherein disposing comprises spraying the graft.

4. The method of claim 3, wherein spraying comprises spraying an inside surface of the vascular graft.

5. The method of claim 4, wherein positioning employs a laser alignment fixture to space the members.

6. The method of claim 5, further comprising creating a plurality of micro-openings through a wall of the vascular graft.

7. The method of claim 1, wherein positioning employs a laser alignment fixture to space the members.

8. The method of claim 7, further comprising creating a plurality of micro-openings through a wall of the vascular graft.

* * * * *